US012616406B2

(12) United States Patent
Myllykangas et al.

(10) Patent No.: US 12,616,406 B2
(45) Date of Patent: May 5, 2026

(54) ELECTRONIC APPARATUS, BIO-SIGNAL MEASUREMENT SYSTEM AND BIO-SIGNAL COUPLING METHOD

(71) Applicant: BITTIUM BIOSIGNALS OY, Kuopio (FI)

(72) Inventors: Juha Myllykangas, Kuopio (FI); Aki Tiihonen, Kuopio (FI); Mikko Määtänniemi, Oulu (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 703 days.

(21) Appl. No.: 17/665,845

(22) Filed: Feb. 7, 2022

(65) Prior Publication Data

US 2023/0248290 A1     Aug. 10, 2023

(51) Int. Cl.
*A61B 5/274*         (2021.01)
*A61B 5/01*          (2006.01)
(Continued)

(52) U.S. Cl.
CPC ............... *A61B 5/274* (2021.01); *A61B 5/01* (2013.01); *A61B 5/02405* (2013.01); *A61B 5/11* (2013.01);
(Continued)

(58) Field of Classification Search
CPC ....... A61B 5/274; A61B 5/01; A61B 5/02405; A61B 5/11; A61B 5/256; A61B 5/28;
(Continued)

(56) References Cited

U.S. PATENT DOCUMENTS

2011/0009824 A1*  1/2011  Yodfat .............. A61M 5/14248
                                                    320/108
2020/0221968 A1*  7/2020  Gumiero ................ A61B 5/282
                          (Continued)

FOREIGN PATENT DOCUMENTS

EP          4 062 832        9/2022
WO     WO-2019118929 A1 *  6/2019  ........... A61B 5/1459

OTHER PUBLICATIONS

May 23, 2023 Search Report issued in European Patent Application 23154368.7, pp. 1-10.

*Primary Examiner* — Linda C Dvorak
*Assistant Examiner* — William Mossbrook
(74) *Attorney, Agent, or Firm* — Nixon & Vanderhye PC

(57)          ABSTRACT
A first electric connector arrangement of an electronic apparatus that is repeatedly connectable with and releasable from a first electric counter-connector arrangement of a bio-signal data processing apparatus. A second electric connector arrangement of the electronic apparatus is connectable with a second electric counter-connector arrangement of the bio-signal electrode arrangement in a releasable manner. A battery provides electric power for operation of the bio-signal data processing apparatus in response to an electric connection through the first electric connector arrangement between the electronic apparatus and the bio-signal data processing apparatus. The first electric connector arrangement includes separate electric connectors, which have multiple pins. The pins are for electric power supply and data transfer. The separate electric connectors and their counter-connectors of the bio-signal data processing apparatus have structural shapes matched with each other for attaching them together based on contact friction in the releasable manner.

16 Claims, 5 Drawing Sheets

(51) Int. Cl.

| | |
|---|---|
| *A61B 5/024* | (2006.01) |
| *A61B 5/11* | (2006.01) |
| *A61B 5/256* | (2021.01) |
| *A61B 5/28* | (2021.01) |
| *A61B 5/291* | (2021.01) |
| *A61B 5/296* | (2021.01) |

(52) U.S. Cl.
CPC ................ *A61B 5/256* (2021.01); *A61B 5/28* (2021.01); *A61B 5/291* (2021.01); *A61B 5/296* (2021.01); *A61B 2560/0214* (2013.01); *A61B 2560/0412* (2013.01)

(58) Field of Classification Search
CPC . A61B 5/291; A61B 5/296; A61B 2560/0214; A61B 2560/0412; A61B 2560/045; A61B 2560/0456; A61B 2562/16; G06F 13/4081; H02J 7/0045
See application file for complete search history.

(56) References Cited

U.S. PATENT DOCUMENTS

| | | | | |
|---|---|---|---|---|
| 2020/0305749 | A1* | 10/2020 | Myllykangas | A61B 5/296 |
| 2021/0251572 | A1* | 8/2021 | Gill | G06F 1/163 |
| 2022/0142476 | A1* | 5/2022 | Nair | A61B 5/344 |

* cited by examiner

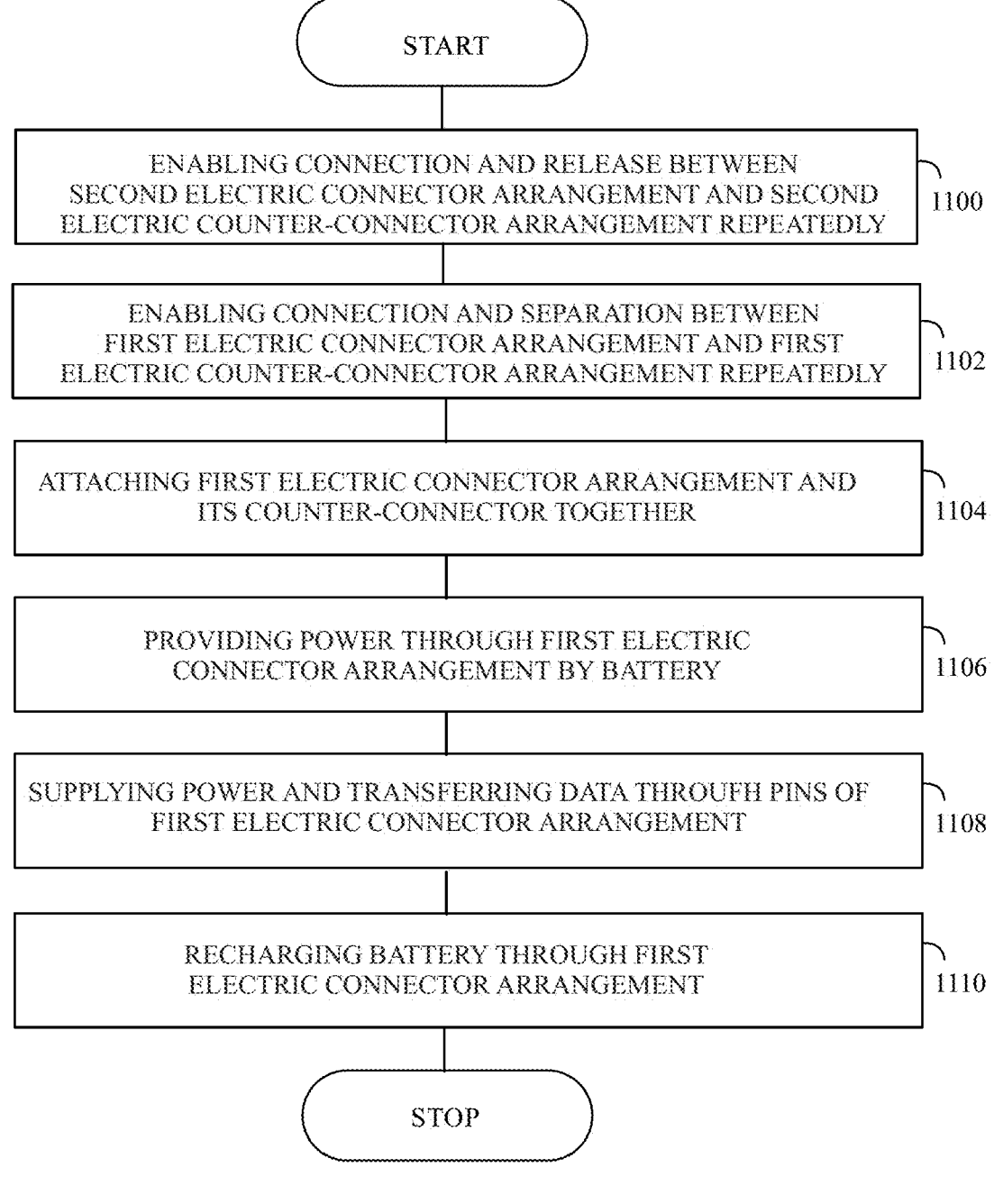

START

ENABLING CONNECTION AND RELEASE BETWEEN
SECOND ELECTRIC CONNECTOR ARRANGEMENT AND SECOND
ELECTRIC COUNTER-CONNECTOR ARRANGEMENT REPEATEDLY          1100

ENABLING CONNECTION AND SEPARATION BETWEEN
FIRST ELECTRIC CONNECTOR ARRANGEMENT AND FIRST
ELECTRIC COUNTER-CONNECTOR ARRANGEMENT REPEATEDLY          1102

ATTACHING FIRST ELECTRIC CONNECTOR ARRANGEMENT AND
ITS COUNTER-CONNECTOR TOGETHER          1104

PROVIDING POWER THROUGH FIRST ELECTRIC
CONNECTOR ARRANGEMENT BY BATTERY          1106

SUPPLYING POWER AND TRANSFERRING DATA THROUFH PINS OF
FIRST ELECTRIC CONNECTOR ARRANGEMENT          1108

RECHARGING BATTERY THROUGH FIRST
ELECTRIC CONNECTOR ARRANGEMENT          1110

STOP

FIG. 11

ELECTRONIC APPARATUS, BIO-SIGNAL MEASUREMENT SYSTEM AND BIO-SIGNAL COUPLING METHOD

FIELD

The invention relates to an electronic apparatus, a bio-signal measurement system and a bio-signal coupling method.

BACKGROUND

In a long-term bio-signal measurement operation time of a battery limits the overall measurement time. In other words, the battery of the bio-signal device needs to be recharged from time to time in order to achieve the needed overall measurement time. The recharging time is typically measured in hours. This is a substantial drawback. Instead of recharging, the bio-signal device, with which the measurement stated, could be replaced by a second bio-signal device with a fresh battery in order to continue the measurement. Because of the long recharging time, it may be necessary to have even a third bio-signal device available to continue the recording of the bio-signal measurement. To have a plurality of bio-signal devices for a single measurement is unpractical, uneconomical and may even be unreliable because of possible failures in connections and handlings. Additionally, releasing one bio-signal device and applying another in its place is also cumbersome. Furthermore, in order to form results from the whole bio-signal measurement it has to be gathered from recordings made by different bio-signal devices.

BRIEF DESCRIPTION

The present invention seeks to provide an improvement for the bio-signal measurements.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which FIG. 1 illustrates an exploded-view drawing of an example an electronic apparatus;

FIG. 11 illustrates of an example of a flow chart of a measuring method.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

The term "about" means that quantities or any numeric values are not exact and typically need not be exact. The reason may be tolerance, resolution, measurement error, rounding off or the like, or a fact that the feature of the solution in this document only requires that the quantity or numeric value is approximately that large. A certain tolerance is always included in real life quantities and numeric values.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 4:
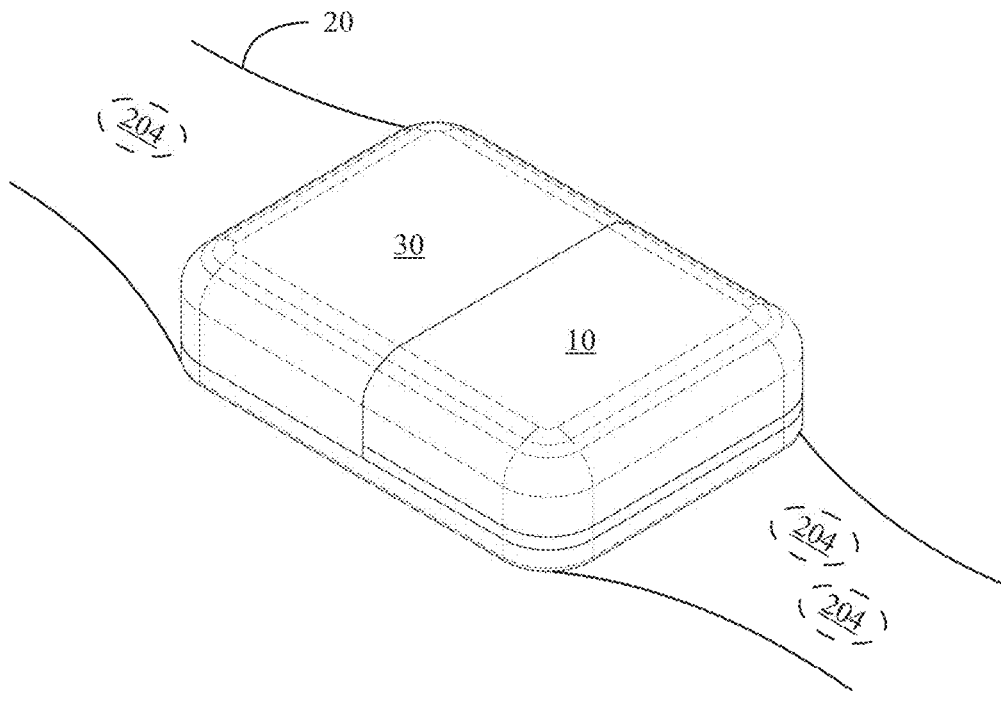
FIG. 4 illustrates an example of the electronic apparatus being in connection with a bio-signal data processing apparatus.
Figure 6:
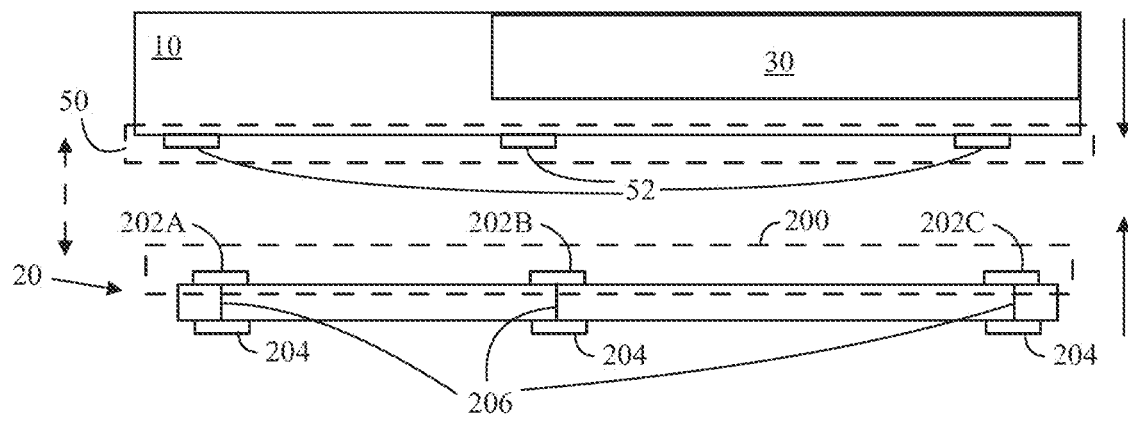
FIG. 6 illustrates an example of a side view of the electronic apparatus being connected with or separated from a bio-signal data processing apparatus.
Figure 7:
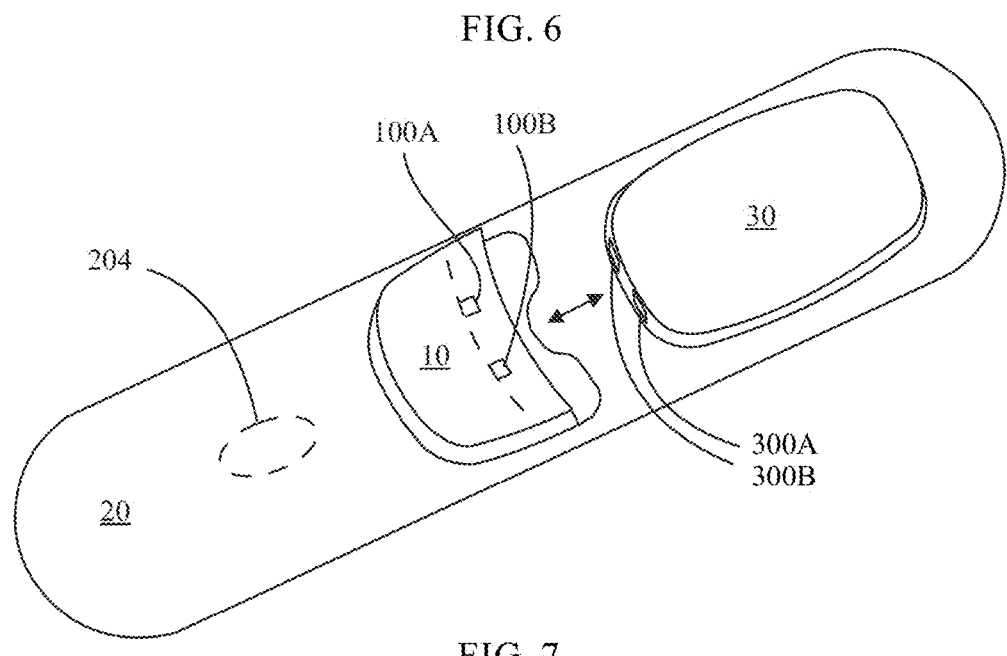
FIG. 7 illustrates an example of connecting counter-connectors of a electric counter-connector arrangement of the bio-signal data processing apparatus and electric connectors of the electronic apparatus with each other, or separating them.

The bio-signal electrode structure 20, which is shown in FIGS. 4, 6 and 7, may be a piece of sheet that may be narrow like a band or broad like a wider planar surface and it is often relatively thin. The dimensions of the bio-signal electrode structure 20 may resemble those of sheet of plastic, paper, board or cloth. The bio-signal electrode structure 20 may also be called a patch electrode structure because of patch electrodes. The bio-signal electrode structure 20 is configured to be attached to skin of a mammal such as a human being and the bio-signal electrode structure 20 has electrodes 204 for a bio-signal measurement. The bio-signal may be related to body movement, body temperature, heart rate variability, electrocardiogram, electromyogram, electroencephalogram or the like for example. During a measurement, the bio-signal electrode structure 20 feeds directly or indirectly electric bio-signals to a non-disposable bio-signal processing device 30 that is separate from the bio-signal electrode structure 20. The disposable bio-signal electrode structure 20 may have a polyethylene terephthalate-layer (PET-layer), for example.

The bio-signal processing device 30, which is shown in FIGS. 1, 2, 3, 4, 5, 6, 7 and 9, may be an electronic device which may convert an analog bio-signal it receives to a digital bio-signal. The bio-signal processing device 30 may also filter the bio-signal in the analog or in the digital form. Additionally or alternatively, the bio-signal processing device 30 may perform data processing of the bio-signal, and it may also store data of the bio-signal and/or a result of its processing. The bio-signal processing device 30 may solely be a digital recording unit, not limiting to this, and in an embodiment the signal processing device 30 may house a very small energy source such as a battery or a capacitor for hot swapping of the electronic apparatus 10 with a battery 102.

Figure 1:
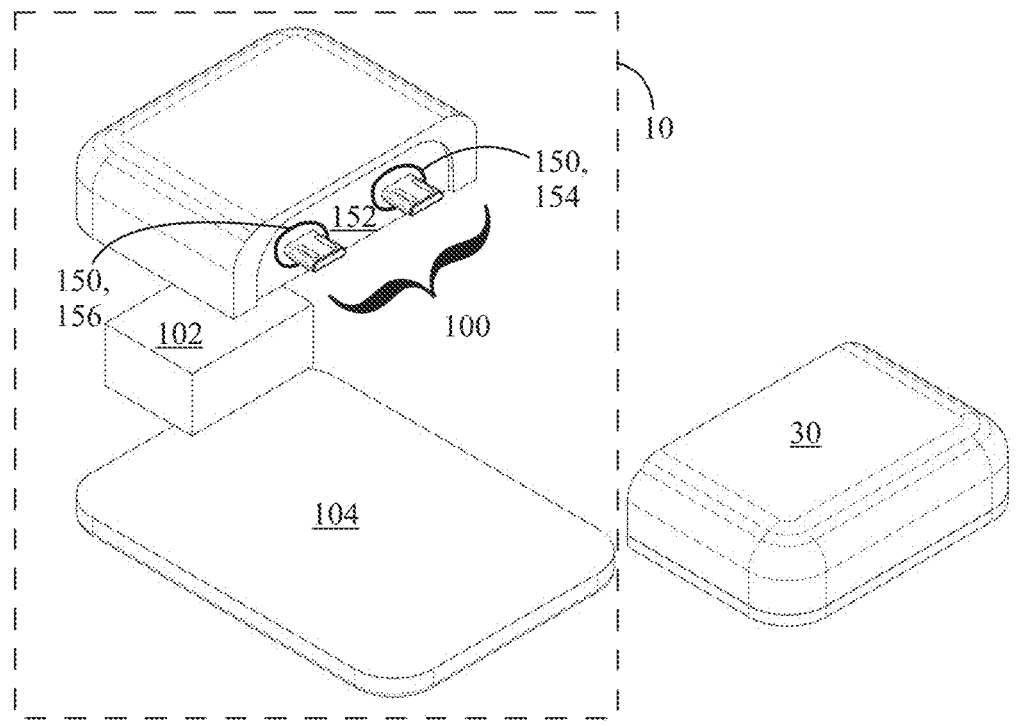

FIG. 1 illustrates an exploded-view drawing of an example of the electronic apparatus 10 connectable simultaneously with a bio-signal electrode arrangement 20 and the bio-signal data processing apparatus 30. The connection between the bio-signal electrode arrangement 20 and the electronic apparatus 10 is not shown in FIG. 1 but the connection is explained in conjunction of FIGS. 6 and 7. The electronic apparatus 10 may be disposable.

The electronic apparatus 10 comprises a first electric connector arrangement 100 that can be repeatedly connected with and released from a first electric counter-connector arrangement 300 of the bio-signal data processing apparatus 30. Because the battery 102 is not in the bio-signal data processing apparatus 30, it may minimize need for maintenance of the bio-signal data processing apparatus 30. It can be considered that the replacement of the battery 102 due to wear out is a part of maintenance and in this solution it can be avoided. The bio-signal data processing apparatus 30 also becomes simpler as it does not need to have a main battery for the whole operation of the bio-signal measurement system.

As the maintenance is simplified, it can be considered that the bio-signal data processing apparatus 30 as such does not require maintenance and it can be made to be maintenance-free. If on the other hand the electronic apparatus 10 requires maintenance, it may be replaced. This is a difference with respect to the prior art where operational features of the bio-signal data processing apparatus 30 and the electronic apparatus 10 are integrated together in an inseparable manner. Alternatively, operational features of the bio-signal electrode structure 20 and the electronic apparatus 10 are integrated together in an inseparably manner in the prior art.

The electronic apparatus 10 comprises the battery 102 that provides electric power for operation of the bio-signal data processing apparatus 30 when the electronic apparatus 10 and the bio-signal data processing apparatus 30 are electrically connected through the first electric connector arrangement 100 with each other. In the prior art, the battery 102 is typically located in the bio-signal data processing apparatus 30, the battery increasing a size, complexity and need for service of the data processing apparatus 30. While the battery 102 is in the electronic apparatus 10, the battery 102 can have more optimal shape and size—it can be much thicker, for example, and therefore house significantly more energy on the same footprint.

The electronic apparatus 10 also comprises a back plate 104 which supports the battery 102 and is in connection with the bio-signal electrode structure 20.

The first electric connector arrangement 100 of the electronic apparatus 10 comprises at least two separate electric connectors 100A, 100B for electric power supply and data transfer between the electronic apparatus 10 and the bio-signal data processing apparatus 30. That there are at least two electric connectors 100A, 100B instead of one increases patient safety because the first electric connector arrangement 100 with the at least two separate electric connectors 100A, 100B is technically a unique electric connector structure which prevents or at least reduces a possibility to have a connection with a different kind of counter-connector which may belong to a potentially hazardous or harmful device.

Figure 2:
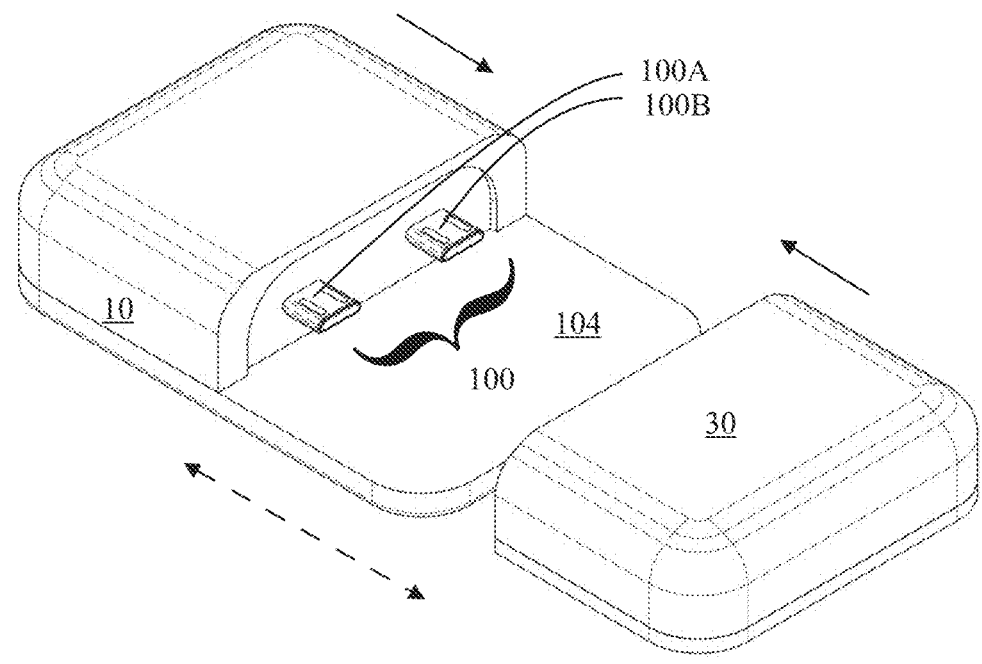
FIGS. 2 and 3 illustrates an example of the electronic apparatus being connected with or separated from a bio-signal data processing apparatus.

In an embodiment an example of which is illustrated in FIGS. 1 and 2, the at least two separate electric connectors 100A, 100B may comprise male universal serial bus connectors, i.e. USB-connectors.

In an embodiment, the at least two separate electric connectors 100A, 100B of the first electric connector arrangement 100 may comprise quick-release electric connectors. An example of the quick-release electric connector is a snap fastener.

FIG. 2 illustrates an example where the electronic apparatus 10 and the bio-signal data processing apparatus 30 are moved toward each other for a connection therebetween (see lines with arrow heads at one end). Alternatively, it can be interpreted that the electronic apparatus 10 and the bio-signal data processing apparatus 30 are moved away from each other after a disconnection therebetween (see dashed line with arrow heads at both ends).

Figure 3:
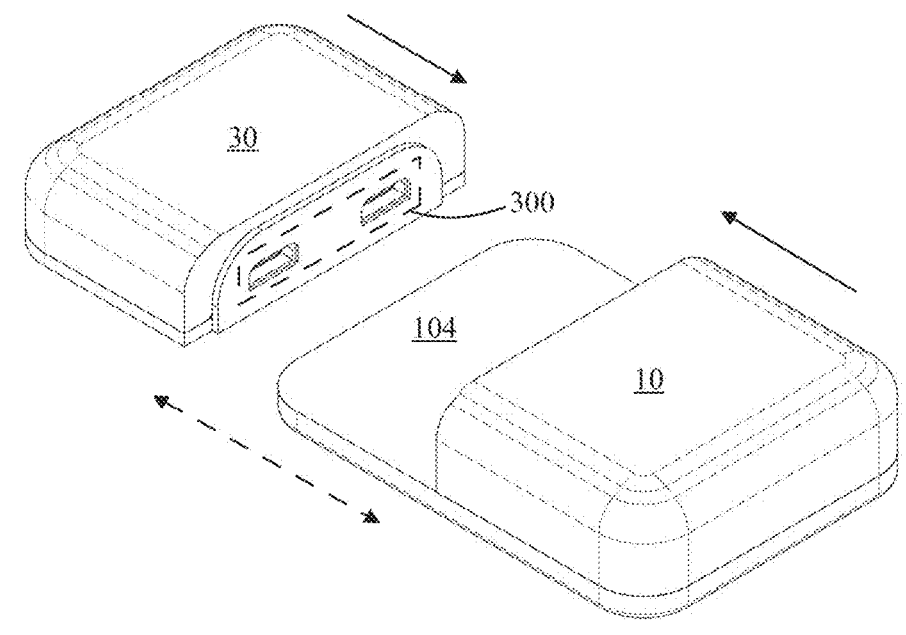

FIG. 3 illustrates an example which shows the counter-connectors 300 of the bio-signal data processing apparatus 30. FIG. 3 also illustrates an example where the electronic apparatus 10 and the bio-signal data processing apparatus 30 are moved toward each other for a connection therebetween (see lines with arrow heads at one end). Alternatively, it can be interpreted that the electronic apparatus 10 and the bio-signal data processing apparatus 30 are moved away from each other after a disconnection therebetween (see dashed line with arrow heads at both ends).

FIG. 4 illustrates an example where the electronic apparatus 10 and the bio-signal data processing apparatus 30 are electrically and physically connected with each other. In this stage, the first electric connector arrangement 100 of the electronic apparatus 10 and the first electric counter-connector arrangement 300 of the bio-signal data processing apparatus 30 are electrically and physically connected with each other.

The at least two separate electric connectors 100A, 100B of the first electric connector arrangement 100 and their counter-connectors 300 of the bio-signal data processing apparatus 30 have structural shapes matched with each other. The matched shapes are configured to attach them together based on contact friction, which keeps them attached together when the person who is wearing the bio-signal measurement system is moving. The retention force is at least doubled due to the at least two electric connectors 100A, 100B. The at least two electric connectors 100A, 100B require more specific insertion angle and make the insertion more implicit, i.e. the coupling can hardly be done in an alternative manner. By using at least two electric connectors 100A, 100B, the battery 102 may be routed such that a current loop does not depend only on one connector which will prevent or at least reduce rusting of the connector in sweaty environment.

The mechanical connection takes place in response to a force pressing the at least two separate electric connectors 100A, 100B of the first electric connector arrangement 100 and their counter-connectors 300 of the bio-signal data processing apparatus 30 in a mechanical contact with each other. Still, the attachment is releasable such that the electronic apparatus 10 can easily, simply and quickly be disconnected from the bio-signal data processing apparatus 30. After the disconnection of the electronic apparatus 10, a new electronic apparatus 10 can be easily, simply and quickly attached to the bio-signal data processing apparatus 30 and the measurement can continue. The replacement can be done in only a few seconds because of simple connectors which are self-aligning and require only pulling and pushing.

Because the battery 102 is in the electronic apparatus 10, the battery is hot-swappable and allows the bio-signal measurement to continue even the battery is swapped. Connection of the electronic apparatus 10 to both the bio-signal data processing apparatus 30 and the bio-signal electrode arrangement 20 is robust enough to handle the everyday use while connection with the electronic apparatus 10 is implicit. The first electric connector arrangement 100 is still minimized.

FIG. 4 also shows electrodes 204 of the bio-signal electrode structure 20 for the bio-signal measurement. The electrodes 204 configured to touch the skin of the person who is wearing the bio-signal measurement system. The electrodes 204 are on an opposite side of the bio-signal electrode structure 20 with respect to the electronic apparatus 10 and the bio-signal data processing apparatus 20, which is illustrated with dashed lines of the electrodes 204 in FIGS. 4 and 7. The locations of the electrodes 204 are not limited to those of FIGS. 4 and 7.

Figure 5:
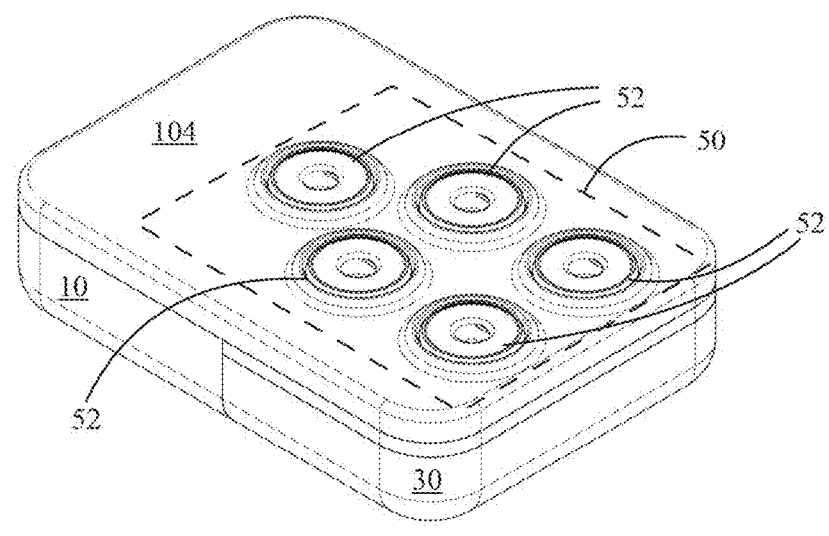
FIG. 5 illustrates an example of a second electric connector arrangement of the electronic apparatus for connecting with a bio-signal electrode structure.

FIG. 5 illustrates an example of the second electric connector arrangement 50 of the electronic apparatus 10. The second electric connector arrangement 50 is configured to be connected with the second electric counter-connector arrangement 200 of the bio-signal electrode arrangement 20 in a releasable manner. In an embodiment, the second electric connector arrangement 50 may comprise connectors 52 that are quick-release electric connectors. In an embodiment, the quick-release electric connectors are a snap fasteners without limiting to that.

FIG. 6 illustrates a side view example of connecting the second electric connector arrangement 50 of the electronic apparatus 10 and the second electric counter-connector arrangement 200 of the bio-signal electrode arrangement 20 with each other (see lines with arrow heads at one end). FIG. 6 can also be interpreted to illustrate an example of disconnecting the second electric connector arrangement 50 of the electronic apparatus 10 and the second electric counter-connector arrangement 200 of the bio-signal electrode arrangement 20 from each other (see dashed line with arrow heads at both ends). The connectors 52 of the electronic apparatus 10 are connected with counter-connectors 202A of the bio-signal electrode arrangement 20. After the connectors 52 of the electronic apparatus 10 have been connected with counter-connectors 202A to 202C of the bio-signal electrode arrangement 20 they can be disconnected from each other for disconnecting the electronic apparatus 10 and the bio-signal electrode arrangement 20 from each other. The counter-connectors 202A of the bio-signal electrode arrangement 20 are connected with the electrodes 204 of the bio-signal electrode arrangement 20 through electric conductors 206.

FIG. 7 also illustrates an example of connecting at least two counter-connectors 300A, 300B of the electric counter-connector arrangement 300 of the bio-signal data processing apparatus 30 and the at least two electric connectors 100A, 100B of the electronic apparatus 10 with each other (see line with arrow heads). In an embodiment, the electronic apparatus 10 may have a shape of a pocket, for example, such that the walls of the electronic apparatus 10 cover partially the bio-signal data processing apparatus 30 when a desired portion of it is inserted into the pocket of the electronic apparatus 10. A size of the pocket may be tightly matched with an outer contour of the electronic apparatus 10 such that it provides protection against splashing of water and dust, for example.

In an embodiment an example of which is illustrated in FIG. 1, the electronic apparatus 10 may comprise a water tight seal 150 on a surface 152 that is configured to be in touch with a surface of the bio-signal data processing apparatus 30 in response to a connection between the electronic apparatus 10 and the bio-signal data processing apparatus 30. In this manner the mechanical structure of the connection between the electronic apparatus 10 and the bio-signal data processing apparatus 30 may meet with IP67 specification (30 min under water in depth of 1 m).

In an embodiment, the water tight seal 150 may comprise a number of separate seal units 154, 156, the number of the separate seal units 154, 156 being the same as the number of the separate electric connectors 100A, 100B of the first electric connector arrangement 100, and the seal units 154, 156 are distributed to the separate electric connectors 100A, 100B such that one seal unit of the seals units 154, 156 is round one of the electric connectors and each of the electric connectors 100A, 100B is encircled by one seal unit. An example of the separate seal units 154, 156 is an O-ring seal.

These kinds of seal arrangements may provide more protection against water and dust for the electric connection may be achieved with the ring seal 150, 154 (see FIG. 1).

Figure 8:
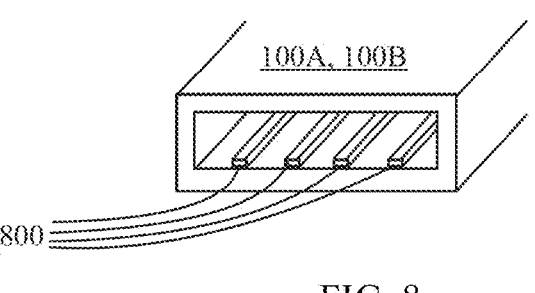
FIG. 8 illustrates an example of at least two separate electric connectors of the electronic apparatus.

FIG. 8 illustrates an example of connectors 100A, 100B. Each of the connectors 100A, 100B may comprise a plurality of pins 800. The pins 800 of the at least two separate electric connectors 100A, 100B may be for electric power supply and data transfer between the electronic apparatus 10 and the bio-signal data processing apparatus 30. By having at least two the electric connectors 100A, 100B, at least double amount of connector pins 800 may be reached and therefore more signals may be routed in and out between the electronic apparatus 10 and the bio-signal data processing apparatus 30.

Figure 9:
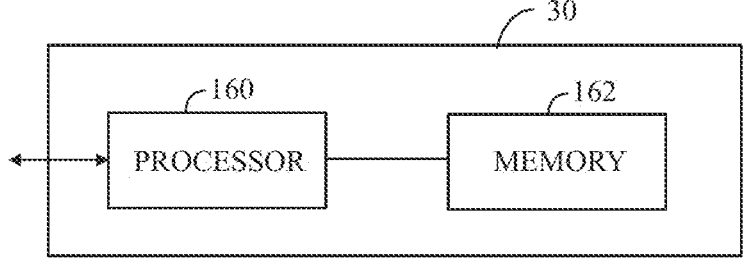
FIG. 9 illustrates an example where the bio-signal processing device has at least one processor and at least one memory.

In an embodiment an example of which is shown in FIG. 9, the bio-signal data processing apparatus 30 may comprise one or more processors 160, and one or more memories 162 that may include a computer program code. The one or more memories 162 and the computer program code may, with the one or more processors 160, cause the data processing apparatus 30 at least to process the bio-signal received from the human or animal.

In an embodiment, the at least two separate electric connectors 100A, 100B of the second electric connector arrangement 50 may comprise quick-release electric connectors. An example of the quick-release electric connector is a snap fastener.

Figure 10:
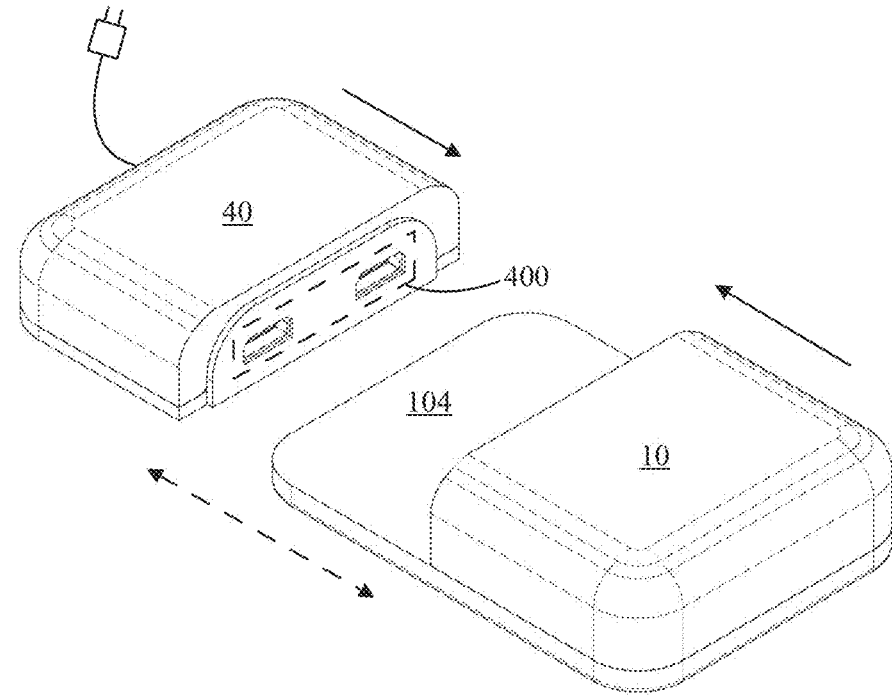
FIG. 10 illustrates an example of recharging a battery of the electronic apparatus.

FIG. 10 illustrates an example of recharging of the battery 102 of the electronic apparatus 10. The electronic apparatus 10 with the battery 102 can be hot-swapped when the battery 102 runs out and the empty battery 102 can be charged on its own while a replacement electronic apparatus 10 is used.

The electronic apparatus 10 may be connected with a recharger 40 which may be connected with an electric socket that, in turn, is connected with an electric power distribution network. That there are the at least two electric connectors 100A, 100B for a connector arrangement 400 of the recharger 40 is a matter of safety because the connection between the recharger 40 and the electronic apparatus 10 is technically unique disallowing or limiting undesirable connection of the electronic apparatus 10 with a different kind of counter-connector. The at least electric connectors 100A, 100B prevent or reduce a possibility to use standard USB cables for recharging the battery 102 in the electronic apparatus 10, for example. Batteries 102 may be recharged in bulk and separately without the bio-signal data processing apparatus 10.

All in all, the electronic apparatus 10 offers improved end customer operation of the bio-signal measurement system. It decreases the cost and enables the production of low-cost, fast changeable energy sources.

FIG. 11 is a flow chart of the bio-signal coupling method. In step 1100, connection and release between a second electric connector arrangement 50 of the electronic apparatus 10 and a second electric counter-connector arrangement 200 of the bio-signal electrode arrangement 20 is enabled repeatedly.

In step 1102, connection and separation of a first electric connector arrangement 100 of an electronic apparatus 10 and a first electric counter-connector arrangement 300 of a bio-signal data processing apparatus 30 is enabled repeatedly. The connection of electronic apparatus 10 with the bio-signal electrode arrangement 20 and the bio-signal data processing apparatus 30 is simultaneous.

In step 1104, the at least two separate electric connectors 100A, 100B of the first electric connector arrangement 100 and their counter-connectors 300 of the bio-signal data processing apparatus 30 are attached together in the releasable manner based on contact friction of structural shapes matched with each other in response to a force pressing the at least two separate electric connectors 100A, 100B of the first electric connector arrangement 100 and their counter-connectors 300 of the bio-signal data processing apparatus 30 in a mechanical contact with each other.

In step 1106 electric power is provided, by a battery 102 of the electronic apparatus 10, for operation of the bio-signal data processing apparatus 30 in response to an electric connection through the first electric connector arrangement 100 between the electronic apparatus 10 and the bio-signal data processing apparatus 30.

In step 1108, electric power is supplied and data is transferred through a plurality of pins 800 of each of the at least two connectors 100A, 100B of the first electric connector arrangement 100.

In an embodiment of step 1110, the battery 102 of the electronic apparatus 10 may be recharged by connecting the first electric connector arrangement 100 of the electronic apparatus 10 with a counter-connector 400 of the recharger 40 for recharging the battery 102 included in the electronic apparatus 10, the counter-connector 400 of the recharger 40 and the first electric connector arrangement 100 of the electronic apparatus 10 enabling repeated connection for recharging.

The method shown in FIG. 11 may be implemented as a logic circuit solution or computer program. The computer program may be placed on a computer program distribution means for the distribution thereof. The computer program distribution means is readable by a data processing device, and it encodes the computer program commands, carries out the operation of the coupling method and optionally controls the processes of the bio-signal measurement system.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

What is claimed is:

1. An electronic apparatus of a bio-signal measurement system, wherein the electronic apparatus comprises:
   a. a first electric connector arrangement comprising at least two separate electric connectors configured to releasably connect to corresponding ones of at least two electric counter-connectors of a first electric counter-connector arrangement of a bio-signal data processing apparatus, the at least two separate electric connectors being configured to engage the at least two electric counter-connectors with a friction fit that maintains a releasable connection during use between the at least two separate electric connectors and the at least two electric counter-connectors, each of the at least two separate electric connectors comprising a plurality of pins configured to supply electric power and transfer data, and the at least two separate electric connectors of the first electric connector arrangement comprising male universal serial bus connectors or quick-release electric connectors;
   b. a second electric connector arrangement configured to releasably connect to a second electric counter-connector arrangement of a bio-signal electrode arrangement;
   c. wherein the at least two separate electric connectors of the first electric connector arrangement are configured to transfer the transferred data, comprising at least a bio-signal acquired by the bio-signal electrode arrangement, between the electronic apparatus and the bio-signal processing apparatus;
   d. a battery configured to provide electric power to the bio-signal data processing apparatus when the electronic apparatus is electrically connected to the bio-signal data processing apparatus through the first electric connector arrangement;
   e. wherein the at least two separate electric connectors of the first electric connector arrangement are configured to each releasably connect to a corresponding counter-connector of a counter-connector arrangement of a recharger for recharging the battery included in the electronic apparatus; and
   f. at least two seal units, each of the at least two seal units being positioned around a corresponding one of at least two separate electric connectors to form a water tight seal with a surface of the bio-signal data processing apparatus when the electronic apparatus is connected to the bio-signal data processing apparatus.

2. The electronic apparatus of claim 1, wherein the at least two separate electric connectors of the first electric connector arrangement comprise male universal serial bus connectors.

3. The electronic apparatus of claim 1, wherein the at least two separate electric connectors of the first electric connector arrangement comprise quick-release electric connectors.

4. The electronic apparatus of claim 1, wherein the number of the at least two seal units is the same as the number of the at least two separate electric connectors of the first electric connector arrangement.

5. The electronic apparatus of claim 1, wherein the at least two separate electric connectors of the first electric connector arrangement are configured to self-align with the at least two electric counter-connectors of the bio-signal data processing apparatus.

6. The electronic apparatus of claim 1, wherein the at least two seal units are distributed to the at least two separate electric connectors of the first electric connector arrangement such that one seal unit of the at least two seals units is round one of the at least two separate electric connectors of the first electric connector arrangement and each of the at least two separate electric connectors of the first electric connector arrangement is encircled by one seal unit in meeting with the IP67 specification.

7. The electronic apparatus of claim 1, wherein the structural shapes of the at least two separate electric connectors of the first electric connector arrangement are unique for preventing or reducing a possibility to have an undesired connection.

8. The electronic apparatus of claim 1, wherein the at least two separate electric connectors of the first electric connector arrangement are configured to be inserted into the at least two electric counter-connectors of the bio-signal data processing apparatus with the friction fit.

9. The electronic apparatus of claim 1, wherein the at least two separate electric connectors of the first electric connector arrangement and the at least two seal units are positioned on a first surface of the electronic apparatus.

10. The electronic apparatus of claim 9, wherein the first surface of the electronic apparatus is recessed relative to a second surface of the electronic apparatus.

11. A bio-signal measurement system comprising a bio-signal data processing apparatus and an electronic apparatus, the electronic apparatus comprising:

g. a first electric connector arrangement comprising at least two separate electric connectors configured to releasably connect to corresponding ones of at least two electric counter-connectors of a first electric counter-connector arrangement of the bio-signal data processing apparatus, the at least two separate electric connectors being configured to engage the at least two electric counter-connectors with a friction fit that maintains a releasable connection during use between the at least two separate electric connectors and the at least two electric counter-connectors, each of the at least two separate electric connectors comprising a plurality of pins configured to supply electric power and transfer data, and the at least two separate electric connectors of the first electric connector arrangement comprising male universal serial bus connectors or quick-release electric connectors;

h. a second electric connector arrangement configured to releasably connect to a second electric counter-connector arrangement of a bio-signal electrode arrangement;

i. wherein the at least two separate electric connectors of the first electric connector arrangement are configured to transfer the transferred data, comprising at least a bio-signal acquired by the bio-signal electrode arrangement, between the electronic apparatus and the bio-signal processing apparatus;

j. a battery configured to provide electric power to the bio-signal data processing apparatus when the electronic apparatus is electrically connected to the bio-signal data processing apparatus through the first electric connector arrangement;

k. wherein the at least two separate electric connectors of the first electric connector arrangement are configured to each releasably connect to a corresponding counter-connector of a counter-connector arrangement of a recharger for recharging the battery included in the electronic apparatus; and l. at least two seal units, each of the at least two seal units being positioned around a corresponding one of at least two separate electric connectors to form a water tight seal a surface of the bio-signal data processing apparatus when the electronic apparatus is connected to the bio-signal data processing apparatus.

12. The bio-signal measurement system of claim 11, wherein at least two separate electric connectors of the second electric connector arrangement comprise quick-release electric connectors.

13. The bio-signal measurement system of claim 11, wherein the structural shapes of the at least two separate electric connectors of the first electric connector arrangement are unique for preventing or reducing a possibility to have an undesired connection.

14. The bio-signal measurement system of claim 11, wherein the at least two separate electric connectors of the first electric connector arrangement are configured to be inserted into the at least two electric counter-connectors of the bio-signal data processing apparatus with the friction fit.

15. A bio-signal coupling method, the method comprising:

m. simultaneously and releasably connecting:

i. at least two separate electric connectors of a first electric connector arrangement of an electronic apparatus to corresponding ones of at least two electric counter-connectors of a first electric counter-connector arrangement of a bio-signal data processing apparatus, the at least two separate electric connectors being configured to engage the at least two electric counter-connectors with a friction fit that maintains a releasable connection during use between the at least two separate electric connectors and the at least two electric counter-connectors, and the at least two separate electric connectors of the first electric connector arrangement comprising male universal serial bus connectors or quick-release electric connectors;

ii. a second electric connector arrangement of the electronic apparatus to a second electric counter-connector arrangement of a bio-signal electrode arrangement;

n. providing, by a battery of the electronic apparatus, electric power for operation of the bio-signal data processing apparatus when the electronic apparatus is electrically connected to the bio-signal data processing apparatus through the first electric connector arrangement;

o. supplying electric power and transferring data through a plurality of pins of each of the at least two separate electric connectors of the first electric connector arrangement;

iii. wherein the at least two separate electric connectors of the first electric connector arrangement transfer the transferred data, comprising at least a bio-signal acquired by the bio-signal electrode arrangement, between the electronic apparatus and the bio-signal processing apparatus;

d. recharging the battery of the electronic apparatus by releasably connecting the at least two separate electric connectors of the first electric connector arrangement to a corresponding counter-connector of a counter-connector arrangement of a recharger for recharging the battery included in the electronic apparatus; and e. sealing with at least two seal units positioned around corresponding ones of at least two separate electric connectors to form a water tight seal with a surface of the bio-signal data processing apparatus when the electronic apparatus is connected to the bio-signal data processing apparatus.

16. The bio-signal coupling method of claim 15, wherein the structural shapes of the at least two separate electric connectors of the first electric connector arrangement are unique for preventing or reducing a possibility to have an undesired connection.

* * * * *